United States Patent

Peuker

[11] 4,408,902
[45] Oct. 11, 1983

[54] METHOD OF AND DEVICE FOR DETERMINING THE BOILING POINT OF A LIQUID

[75] Inventor: Karl Peuker, Ebern, Fed. Rep. of Germany

[73] Assignee: Fag Kugelfischer Georg Schäfer & Co., Schweinfurt, Fed. Rep. of Germany

[21] Appl. No.: 339,104

[22] Filed: Jan. 13, 1982

[30] Foreign Application Priority Data

Jan. 17, 1981 [EP] European Pat. Off. ........ 81100334.2

[51] Int. Cl.³ ............................................. G01N 25/08
[52] U.S. Cl. ........................................ 374/27; 73/61.3
[58] Field of Search .............................. 374/27, 25, 16; 73/61.3

[56] References Cited

U.S. PATENT DOCUMENTS

| | | | |
|---|---|---|---|
| 3,084,535 | 4/1963 | Markey | 374/27 |
| 3,253,454 | 5/1966 | Neil | 374/27 |
| 3,446,056 | 5/1969 | Koch | 374/27 |
| 3,564,900 | 2/1971 | André et al. | 374/25 |

Primary Examiner—E. R. Kazenske
Assistant Examiner—Joseph W. Roskos
Attorney, Agent, or Firm—Karl F. Ross

[57] ABSTRACT

In order to determine the boiling point of a liquid, especially a nonaqueous one such as a brake fluid, a device suspended in a body of that liquid—e.g. in a reservoir supplying fluid to a brake cylinder—forms a narrow chamber which is downwardly open and upwardly closed and which contains means for heating the liquid in that chamber and measuring its temperature; the two functions can be simultaneously performed by a thermistor. When the boiling point is reached and the liquid in the chamber is vaporized, a lessening of the heat conduction to the main body of liquid results in a steep rise in temperature; the boiling point marked by this event can be read on a meter and/or qualitatively indicated by differently colored lights, for example. An excessive temperature rise early in the test will also show an unduly low liquid level in the reservoir.

9 Claims, 5 Drawing Figures

METHOD OF AND DEVICE FOR DETERMINING THE BOILING POINT OF A LIQUID

FIELD OF THE INVENTION

My present invention relates to a method of and a device for determining the boiling point of a liquid, especially a nonaqueous one such as the brake fluid of an automotive vehicle.

BACKGROUND OF THE INVENTION

A known device for testing a brake fluid and detecting its boiling point comprises a heating cup into which some of the fluid is injected with the aid of a syringe. After being closed against the atmosphere, the cup is heated until evolving gas bubbles begin to pass through a U-shaped tube into a receptacle therefor. The temperature at which this occurs is noted as the boiling point, whereupon the liquid in the cup is returned to the brake system of the vehicle by means of the same syringe; both the cup and the syringe are then carefully cleansed preparatorily to a new test. Such a device is relatively expensive and cumbersome to handle, being thus not very well suited for use in a repair shop for automotive vehicles.

OBJECTS OF THE INVENTION

The general object of my present invention, therefore, is to provide an improved method of determining the boiling point of such a liquid which can be carried out by simple means in a shop or even on the street by unskilled personnel.

A more particular object is to provide a device for performing such boiling-point determinations in situ, e.g. directly on an automotive vehicle or on a reservoir containing the liquid to be tested.

SUMMARY OF THE INVENTION

In accordance with the method aspect of my invention, a quantity of the liquid to be tested is confined in a space which is closed at the top and is in communication at its bottom with a larger body of the same liquid. During gradual heating of the liquid so confined, the temperature in the space is continuously measured. When that liquid begins to boil, the rate of temperature rise undergoes a significant change; thus, if the temperature is measured near the top of a narrow test space from which the liquid is quickly displaced by evolving vapors, the heat generated in the vicinity of the sensor used for the temperature measurement is less rapidly conducted to the larger body of liquid so that the rate of temperature rise undergoes a steep increase. Such a rate change is taken as an indication that the boiling point has been reached.

If for any reason the testing space is insufficiently filled with liquid at the beginning of the heating operation, such a steep temperature rise will occur early in the test. Thus, a comparison of the initial rate of temperature increase with a reference value may be used for ascertaining a possible absence of liquid in that space.

In structural terms, my invention is implemented by a device comprising a probe suspended in a container for the liquid to be tested, this probe being a heat-insulated chamber which is closable at the top against the atmosphere and is open at the bottom for communication with the interior of the container below whose normal liquid level the chamber is located. The chamber contains heating and temperature-measuring means connected to external display means for signaling the aforementioned rate change as an indication that the boiling point of the liquid has been reached.

The heating and temperature-measuring means may be combined into a single unit, specifically a thermistor connected across a source of substantially constant voltage. The current drawn by the thermistor will heat the liquid and will also serve as a temperature-indicating parameter.

BRIEF DESCRIPTION OF THE DRAWING

The above and other features of my invention will now be described in detail with reference to the accompanying drawing in which.

SPECIFIC DESCRIPTION

Figure 1:
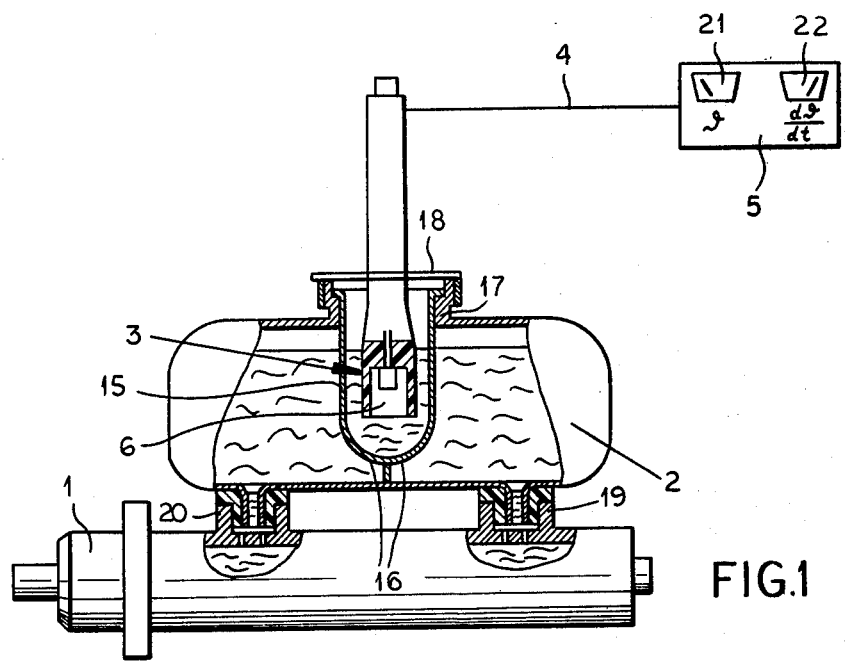
FIG. 1 is a somewhat diagrammatic, partly sectional side-elevational view of a device embodying my invention.
Figure 3:
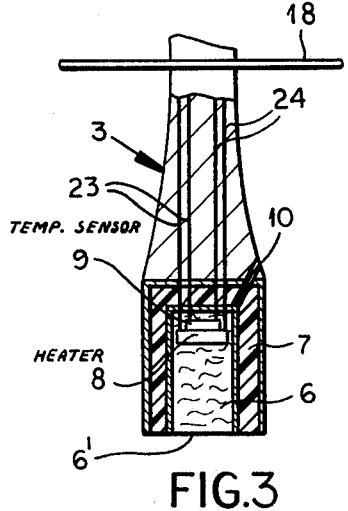
FIGS. 3-5 are sectional detail views, drawn to a larger scale, of a probe forming part of the device of FIG. 1.
Figure 4:
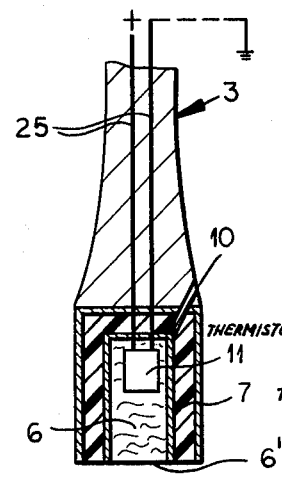

In FIG. 1 I have shown a vessel 1, e.g. the main cylinder of an automotive brake system, supplied with brake fluid from an overlying reservoir 2 by way of tubular supports 19 and 20. A container 15 with bottom openings 16, immersed in the liquid, is supported by a flange 17 formed at the top of that reservoir. A probe 3, more fully described hereinafter with reference to FIGS. 3 and 4, is rigid with a lid 18 and is suspended inside container 15 when that lid comes to rest upon flange 17. Probe 3 forms a downwardly open chamber 6 which lies below the liquid level in reservoir 2.

As shown in FIGS. 3 and 4, the preferably cylindrical chamber 6 is surrounded at its periphery and at the top by heat-insulated walls 7 of plastic material which may be internally and externally coated with a protective layer. A vent 10 in the roof of chamber 6 enables the escape of air through a gap between flange 17 and lid 18 when the probe is slowly lowered into the container 15 so that the surrounding liquid enters the chamber through its opening bottom 6'. In the working position illustrated in FIG. 1, chamber 6 is shielded against the atmosphere so that evolving vapors will be substantially confined therein and will expel some of its liquid through the open bottom 6'. Means could also be provided for directly closing the vent 10.

FIG. 3 further shows a heater 8 and a temperature sensor 9 disposed in the upper end of the chamber so as to be surrounded with small clearance by its walls 7. Heater 8 and sensor 9 are connected by respective wire pairs 23 and 24, forming part of a cable 4 shown in FIG. 1, to a display panel 5 provided with a temperature indicator 21 and a temperature-rise indicator 22.

Figure 2:
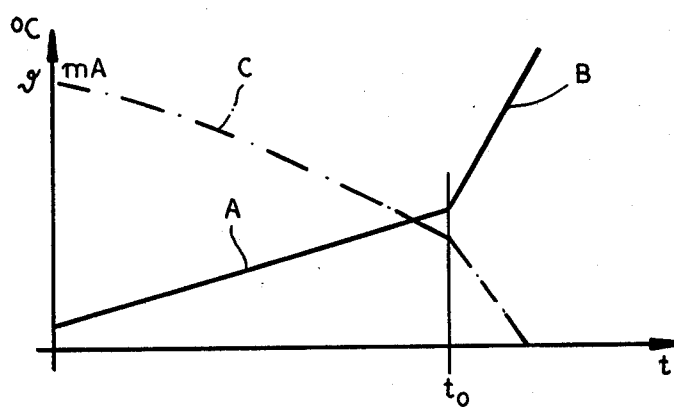
FIG. 2 is a graph showing temperature as a function of time in the practice of my present method.

When the heater 8 is energized, the temperature $\theta$ measured by sensor 9 will rise gradually and substantially linearly as indicated at A in FIG. 2. When the boiling point of the liquid is reached, i.e. at a time $t_o$, the liquid in the clearance surrounding the elements 8 and 9 quickly evaporates so that the heat generated by element 8 is no longer dissipated as quickly as before to the main body of liquid occupying the surrounding container 15 and the reservoir 2. This results in a rapid increase in the temperature gradient $d\theta/dt$ as represented by a line B in FIG. 2 and as visualized by indicator 22; the operator, on noting that increase, reads the boiling point on indicator 21. The calculation of the temperature gradient can be performed electronically with the aid of a nonillustrated timer (e.g. a pulse generator) also included in display panel 5.

Figure 5:
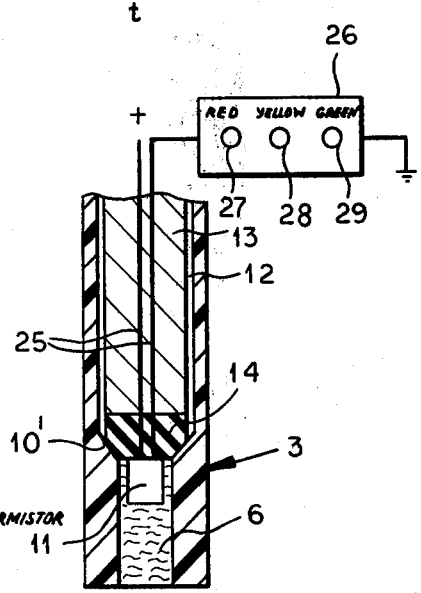

As shown in FIG. 4, the heater 8 and the temperature sensor 9 of FIG. 3 can be combined into a single unit 11, namely a thermistor connected by a pair of leads 25 across a source of substantially constant voltage schematically represented in FIGS. 4 and 5. This connection may include a visual indicator such as the one shown at 21 in FIG. 1, responsive to the current flow in line 25, as well as a companion indicator 22 controlled by electronic circuitry deriving the temperature gradient from the change in current flow; with use of either a positive or a negative thermistor, the relationship between the current and the temperature will be nonlinear. A positive thermistor, for example, may draw a current conforming to a curve C shown in FIG. 2, with a sharp bend at the boiling point represented by instant $t_o$.

The display panel 5 of FIG. 1 may also be replaced by a different indicator 26, as shown in FIG. 5, whose electronic circuitry includes several threshold comparators energizing respective light sources if the boiling point is found to lie above, at, or below the critical value. Thus, for example, a light-emitting diode 27 may glow red when the boiling point lies in an "unsatisfactory" range below the critical level, the light of another such diode 28 indicating by a yellow color a "barely acceptable" value close to that critical level, whereas green light from a third diode 29 may show a "safe" range well above that level. The indicator 26 of FIG. 5 may be used also with the heater 8 and the temperature sensor 9 of FIG. 3.

FIG. 5 further shows a modified probe 3' whose cylindrical walls form an annular shoulder 10' above chamber 6 on which a thermally insulating plug 14 carried by a stem 13 comes to rest in the working position. The stem 13 is raised during immersion of the probe into the liquid to provide a gap through which air can escape from chamber 6. This structure, of course, could also be used with separate heating and temperature-sensing elements as shown in FIG. 3.

If the heating and temperature-measuring means 8, 9 or 11 were disposed farther down in chamber 6, or if the surrounding clearance were considerably widened, the temperature sensor would remain immersed in the boiling liquid for an extended period while registering a virtually constant surrounding temperature. In such a case, therefore, an indicator as shown in FIG. 1 or FIG. 5 could be made responsive to a leveling of the temperature curve; such a leveling will actually occur also in the graphs of FIG. 2 but has not been illustrated there on account of its short duration.

For convenience, the visual indicator 5 or 26 may be mounted directly on the lid 18 of probe 3 or on a similar cover of probe 3'.

I claim:

1. A method of determining the boiling point of a liquid, comprising the steps of:
   (a) confining a quantity of the liquid to be tested in a space closed at the top and in communication at the bottom with a larger body of the same liquid;
   (b) gradually heating the liquid in said space;
   (c) continuously measuring the temperature in said space during the heating step; and
   (d) registering the occurrence of a significant change in the rate of temperature rise measured in step (c) as an indication of the boiling point of the liquid having been reached.

2. A method as defined in claim 1, comprising the further step of comparing an initial rate of temperature rise with a reference value for ascertaining a possible absence of liquid in said space.

3. A method as defined in claim 1 or 2 wherein the measuring of temperature in step (c) is performed at a location close to the top of said space from which the liquid is rapidly displaced by evolving vapors upon reaching the boiling point, thereby causing a steep temperature rise registered in step (d).

4. A device for determining the boiling point of a liquid, comprising:
   a probe suspended in a container for the liquid to be tested, said probe having a heat-insulated chamber closable at the top against the atmosphere and open at the bottom for communication with the interior of the container, said chamber lying below the normal liquid level of the container;
   heating and temperature-measuring means disposed in said chamber for contact with liquid entering same from said container; and
   external display means connected to said heating and temperature-measuring means for signaling a significant change in chamber temperature as an indication that the boiling point of the liquid has been reached.

5. A device as defined in claim 4 wherein said heating and temperature-measuring means comprises a thermistor connected across a source of substantially constant voltage.

6. A device as defined in claim 4 or 5 wherein said chamber is provided with a sealable vent.

7. A device as defined in claim 6 wherein said probe comprises a cylindrical wall surrounding said chamber and forming an annular shoulder at the top of said chamber, said vent being an annular channel formed between said wall and a plug normally resting on said shoulder.

8. A device as defined in claim 4 or 5 wherein said display means comprises electronically controlled light-emitting diodes indicating different boiling-point ranges above, at and below a critical level.

9. A device as defined in claim 4 or 5 wherein said heating and temperature-measuring means is disposed near the top of said chamber and is surrounded by a narrow clearance enabling a rapid displacement of liquid therefrom by evolving vapors upon attainment of the boiling point, said display means being responsive to a steep rise in the temperature measured in said clearance for indicating said boiling point.

* * * * *